United States Patent [19]

Fumagalli et al.

[11] Patent Number: 5,250,724
[45] Date of Patent: Oct. 5, 1993

[54] PROCESS FOR THE PREPARATION OF TRIMELLITIC ACID

[75] Inventors: Carlo Fumagalli, Valbremo; Lorenzo Capitanio, Mozzo; Giancarlo Stefani, Gorle, all of Italy

[73] Assignee: Alusuisse Italia S.p.A., Milan, Italy

[21] Appl. No.: 881,812

[22] Filed: May 12, 1992

[30] Foreign Application Priority Data

May 17, 1991 [IT] Italy .................. MI 91A001360

[51] Int. Cl.$^5$ .............................. C07C 51/265
[52] U.S. Cl. .................... 562/416; 549/245; 562/417; 562/480
[58] Field of Search ............ 562/416, 417, 480; 549/245

[56] References Cited

U.S. PATENT DOCUMENTS

| | | | |
|---|---|---|---|
| 2,833,816 | 5/1958 | Saffer et al. | 562/413 |
| 3,683,016 | 8/1972 | Darin et al. | 562/417 |
| 4,755,622 | 7/1988 | Schammel et al. | 562/413 |
| 4,895,978 | 1/1990 | Darin et al. | 562/416 |
| 4,948,921 | 8/1990 | Green et al. | 562/413 |
| 4,992,579 | 2/1991 | Schammel | 562/413 |
| 5,095,141 | 3/1992 | Schammel et al. | 562/414 |

OTHER PUBLICATIONS

Ullmann's Encyklopadie der techn. Chemie, 4th Ed., vol. 9, p. 150, (1972–1975).

Primary Examiner—José G. Dees
Assistant Examiner—Vera C. Clarke
Attorney, Agent, or Firm—Fisher, Christen & Sabol

[57] ABSTRACT

A very selective process for the catalytic air oxidation of pseudocumene to trimellitic acid. Manganese, cobalt, cerium and titanium in the presence of bromine are used as the catalyst.

15 Claims, No Drawings

PROCESS FOR THE PREPARATION OF TRIMELLITIC ACID

BACKGROUND OF THE INVENTION

1. Field of the Invention

The invention relates to a novel process for the catalytic oxidation of pseudocumene to trimellitic acid.

2. Background Art

Trimellitic acid is employed in the plastics industry as an intermediate for the preparation of synthetic resins, plasticisers, etc. Frequently, the trimellitic acid is reacted directly via a dehydration step to give trimellitic anhydride which, in turn, is widely used as an intermediate in the plastic industry, in particular in the preparation of polyesters.

Numerous catalytic oxidation processes are known in order to react pseudocumene to give trimellitic acid. Thus, it already follows from U.S. Pat. No. 2,833,816 to oxidize polyalkylaromatic compounds, such as, trimethylbenzenes, in the presence of cobalt, manganese, cerium and bromine to give the corresponding polycarboxylic acids. However, it was only possible to achieve a yield of 52.5 mol percent for the reaction of pseudocumene to give trimellitic acid. According to U.S. Pat. No. 3,683,016, it was possible to increase this yield by adding a cobalt/manganese/cerium/bromine catalyst stepwise to the oxidation of pseudocumene. As Comparison Example A below shows, it was possible to increase the yield considerably even if the values of the process according to the invention of this application were not attained. A serious disadvantage, however, was the low selectivity of this known process, which led to an increased secondary product formation and thus showed itself by a considerable discoloration of the product in the further reaction to give the anhydride. It was also attempted to replace cerium by zirconium. It thus follows, for example, from U.S. Pat. No. 4,755,622, to react pseudocumene to give trimellitic acid or further to give the anhydride using a cobalt/manganese/zirconium/bromine catalyst. As Comparison Example B below shows, the yield of the known process is only slightly below the values of the process according to the invention of this application. A considerable disadvantage is again the selectivity, which leads to relatively high secondary product formation and thus leads to considerable discoloration of the product in the direct further reaction of the acid to give the anhydride.

Since, as mentioned above, trimellitic anhydride is employed for the preparation of polyesters, an inferior quality of the starting materials considerably influences the properties of the polyester prepared therefrom.

BROAD DESCRIPTION OF THE INVENTION

The main object of the invention is to provide a process in which pseudocumene can be reacted to give trimellitic acid very selectively and with a high yield. Other objects and advantages of the invention are set out herein or obvious herefrom to one skilled in the art.

The objects and advantages of the invention are achieved by the processes of the invention.

The invention involves a process for the preparation of trimellitic acid by the catalytic oxidation of pseudocumene with air in acetic acid as a solvent and in the presence of cobalt, manganese, cerium, titanium and bromine as a catalyst.

Preferably the total metal concentration, comprising cobalt, manganese, cerium and titanium, is between 0.1 and 1 percent by weight, relative to pseudocumene. Preferably the titanium content is between 0.5 and 10 percent by weight, relative to the total metal concentration. Preferably the cobalt content is between 20 and 60 percent by weight, relative to the total metal concentration. Preferably the manganese content is between 10 and 50 percent by weight, relative to the total metal concentration. Preferably the cerium content is between 5 and 30 percent by weight, relative to the total metal concentration. Preferably 0.05 to 0.7 percent by weight of bromine is employed, relative to pseudocumene. Preferably the ratio of acetic acid to pseudocumene is between 1 to 1 and 4 to 1. Preferably the reaction is carried out at a reaction temperature between 140° and 240° C. and at a pressure between 5 and 30 bars.

The invention also involves the use of trimellitic acid, prepared according to the production process of the invention, for the preparation of high purity trimellitic anhydride.

DETAILED DESCRIPTION OF THE INVENTION

In the invention process for preparing trimellitic acid, pseudocumene is oxidized with air in acetic acid as a solvent and in the presence of cobalt, manganese, cerium and bromine and, according to the invention, additionally using titanium, to give trimellitic acid. Surprisingly, an increased selectivity, synonymously with a reduction in secondary product formation, in high yield was achieved by means of the additional catalyst component titanium.

The starting material of the process according to the invention is expediently an industrial pseudocumene. The solvent acetic acid can contain up to 10 weight percent of water and is customarily employed in a weight ratio of acetic acid to pseudocumene of 1:1 to 4:1, preferably 1.5:1 to 3.0:1. The process according to the invention is expediently carried out such that the total metal concentration (Co, Mn, Ce and Ti), relative to pseudocumene, is between 01 and 1 percent by weight, preferably between 0.20 and 0.55 percent by weight. The bromine concentration, relative to pseudocumene, expediently varies between 0.05 and 0.7 percent by weight, preferably between 0.1 and 0.3 percent by weight. Relative to the total metal concentration, the concentrations of the individual metal components advantageously vary within the following ranges:

Cobalt 20 to 60 percent by weight, preferably 35 to 55 percent by weight

Manganese: 10 to 50 percent by weight, preferably 20 to 40 percent by weight

Cerium: 5 to 30 percent by weight, preferably 10 to 25 percent by weight

Titanium: 0.5 to 10 percent by weight, preferably 1 to 7 percent by weight.

The metal catalysts are expediently employed in the form of suitable organometallic compounds or in the form of salts which are easily available and soluble in acetic acid, that is to say, for example, cobalt in the form of the acetate, manganese in the form of the acetate or chloride, and cerium and titanium in the form of the chloride. Bromine is also customarily not employed in elementary form, but in the form of suitable organic or inorganic compounds. Bromides, such as, ammonium bromide or hydrogen bromide, are advantageously employed.

The addition of catalyst can either be carried out by initially introducing the total amount of the metal catalysts and bromine before the beginning of the reaction, or by adding the catalyst composition and the amount of catalyst according to the course of the reaction. Advantageously, the catalyst composition and the amount of catalyst are added according to the course of the reaction. In a preferred variant, for example, the reaction is initiated using a starting amount of a catalyst composition of cobalt, manganese, titanium and bromine, the total amount of cobalt already being present and the remaining amount of manganese, titanium, bromine and cerium being added stepwise or continuously in the course of the reaction.

The oxidation of pseudocumene to trimellitic acid takes place in a temperature range from 140° to 240° C., preferably between 150° and 220° C., and at appropriate pressures between 5 and 30 bar, preferably between 6 and 25 bar. The oxidizing agent is advantageously air, although one can use oxidizing agents with different oxygen content. To avoid formation of explosive mixtures, oxygen in the off gases is preferably kept below 8 percent volume.

The reaction is as a rule complete after 50 to 100 minutes. Yields of over 90 mol percent can be achieved using the process according to the invention.

The trimellitic acid formed by the process according to the invention already has a very high purity (low secondary product formation) so that it can be subjected directly to thermal dehydration to give trimellitic anhydride without a special purification step. This dehydration step is known from the literature [see, for example, *Ullmann's Encyklopadie der techn. Chemie*, (Ullmann's Encyclopaedia of Industrial Chemistry), 4th edition, Vol. 9, p. 150] and expediently comprises a thermal dehydration step at 220° to 230° C. and a subsequent vacuum distillation of the resulting trimellitic anhydride. In comparison to the known processes, the trimellitic anhydride obtained via the trimellitic acid prepared according to the invention has a demonstrably better quality, which is shown by a substantially lower intrinsic coloration and a better quality of the polyesters prepared therefrom.

EXAMPLES

Introduction

The following experiments were carried out in a customarily equipped 5 liter titanium autoclave. During the experiments, continuous measurement of $O_2$, CO and $CO_2$ in the off gases was ensured. Oxygen concentration in the off gases was kept below 8 percent by volume. The crude trimellitic acid obtained was dehydrated directly, according to Example 1, to give trimellitic anhydride. The latter was subjected to the following quality tests:

Resin test: 15 g of the respective trimellitic anhydride and 20 g of ethylene glycol were put into a glass cylinder of the dimensions:

diameter 20 mm, height 200 mm and the mixture was polymerized at 200° C. ±5 percent in an electrically heated aluminum block during the course of 60 minutes.

The coloration of the polyester resin obtained was measured according to the APHA or Hazen color test according to ASTM-D 1209-62 in Hz (Hazen). A lower Hz value, for example, 20 to 40, in this case means a slight coloration, while a higher value, for example, 80 and higher, already points to a considerably discolored product.

The molten trimellitic anhydride was subjected to the same color test.

EXAMPLE 1

540 g of pseudocumene was initially introduced into the reactor containing 1080 g of acetic acid ($H_2O$ content 45 g). The starting amount of catalyst, containing cobalt in the form of the acetate, manganese in the form of the acetate and titanium in the form of the chloride, was initially introduced in the ratio of Co 62 percent by weight, Mn 35.5 percent by weight and Ti 2.5 percent by weight (metal concentration of 0.233 percent by weight, relative to the pseudocumene). The starting amount of bromine in the form of ammonium bromide was initially introduced in an amount of 0.039 percent by weight of bromine, relative to pseudocumene. The reaction mixture was heated under nitrogen with stirring. Air was introduced at a pressure of about 6 bar from 160° C. The reaction temperature was then increased stepwise to 210° C. in the course of 40 minutes, synchronized with a pressure increase of 23 bar. 10 min after the start of the reaction, a catalyst solution in acetic acid containing Mn, Ti and Ce in the weight ratio of Sep. 9, 1982 in the form of the appropriate salts and 0.14 percent by weight of bromine, relative to pseudocumene, was added continuously during the course of 50 minutes. The amount of metal catalyst continuously added, relative to pseudocumene, was 0.076 percent by weight. The total metal concentration (starting amount + amount added) was thus 0.31 percent by weight, relative to pseudocumene. The total amount of bromine, relative to pseudocumene, was 0.178 percent by weight. After a reaction time of 65 minutes the oxygen content in the waste off gases reached 8 percent volume, the reaction was discontinued, the reaction mixture was cooled to 50° C. and the resultant slurry was filtered. Relative to the pseudocumene employed, a yield according to HPLC of 91.5 mol percent was achieved. The secondary product relative to the pseudocumene employed was determined to be 3.1 mol percent; CO and $CO_2$ to be 5.4 mol percent. The still moist filter cake was directly further treated to give trimellitic anhydride. To do this, the trimellitic acid was dehydrated thermally at 220° C. during the course of 3 hours and the resultant anhydride was then subjected to a vacuum distillation at 10 mm Hg. The resultant trimellitic anhydride had a melting point of 168.9° C. The color of the product in the molten state was 60 Hz. The resin test gave a value of 20 Hz. The results are summarized in the Table below.

EXAMPLE 2

The reaction was carried out according to Example 1, but with a changed starting catalyst composition of Co to Mn to Ti of 60 percent by weight/39 percent by weight/1 percent by weight and a changed catalyst composition during the continuous addition of Mn to Ti to Ce of 10 percent by weight/4 percent by weight/86 percent by weight. The reaction lasted 72 minutes. The results are shown in the Table below.

EXAMPLE 3

The reaction was carried out according to Example 1, but with a changed starting catalyst composition of Co to Mn to Ti of 61 percent by weight/35 percent by weight/4 percent by weight and a changed catalyst composition during the continuous addition of Mn to Ti to Ce of 9 percent by weight/14 percent by weight/77 percent by weight. The reaction lasted 60 minutes. The results are shown in the Table below.

EXAMPLE 4

The reaction was carried out according to Example 1, but with a weight ratio acetic acid/pseudocumene of 3:1 instead of 2:1. In the same apparatus used in Example 1, 420 g of pseudocumene was charged into 1260 g of acetic acid containing 53 g of water. The composition of the initial catalyst and of the catalyst added during the oxidation was the same as in Example 1. The total metal concentration (initial plus added) was 0.31 percent by weight, and the total amount of bromine, relative to pseudocumene, was 0.179 percent by weight. The introduction of air was started at 155° C. and at a pressure of 10 bar. The reaction temperature was increased stepwise to 210° C. over the course of 40 minutes. During the course of this, the pressure rose to 27 bar. The catalyst solution mentioned in Example 1 was added 10 minutes after the start of the reaction. The reaction was complete after 70 minutes. It was possible to obtain a yield of acid of 91.7 mol percent. The results are shown in the Table below.

COMPARISON EXAMPLE A (According to U.S. Pat. No. 3,683,016, Example 1)

Co/Mn/Ce Catalyst Without Titanium 385 g of pseudocumene and 1235 g of acetic acid were initially introduced with a Co/Mn/Ce catalyst, consisting of 10 percent by weight of Ce, 10 percent by weight of Mn and 80 percent by weight of Co such that the total metal concentration, relative to pseudocumene, was 0.22 percent by weight. 0.8 percent by weight of bromine, relative to pseudocumene, was also added. The reaction mixture was heated to 185° C. (365° F.) (pressure 9 bar), after which air was introduced. The temperature was increased to 206° C. during the course of 50 minutes. During the course of this temperature increase, the pressure rose to 28 bar. A catalyst solution, containing 0.12 percent by weight of Mn and 0.03 percent by weight of Ce and 0.9 percent by weight of bromine (weight relative to pseudocumene) was added 30 minutes after the start of the reaction. The reaction was complete after a reaction time of 65 minutes. The results are shown in the Table below.

COMPARISON EXAMPLE B (According to U.S. Pat. No. 4,755,622, Example 1)

Co/Mn/Zr Catalyst Without Titanium 580 g of pseudocumene and 1030 g of acetic acid (containing 54 g of water) were initially introduced into the reactor with a Co/Mn/Zr/Br catalyst, containing 0.0173 g atom of cobalt, 0.00465 g atom of manganese, 0.000385 g atom of zirconium and 0.00336 mol of HBr. The reaction mixture was heated to 160° C. and the pressure set at 10 bar, after which air was introduced. 0.0111 mol of HBr, 0.000919 mol of manganese and 0.000281 mol of zirconium were added in the course of the oxidation. The reaction temperature was increased to 210° C., and the pressure to 28 bar, in the course of the reaction. The reaction was complete after 70 minutes. The results are summarized in the Table below.

TABLE

| | | Example | | | | | |
|---|---|---|---|---|---|---|---|
| | | 1 | 2 | 3 | 4 | A | B |
| Yield of trimellitic acid | mol % | 91.5 | 91.6 | 91.0 | 91.7 | 89.1 | 90.0 |
| Secondary products | mol % | 3.1 | 3.4 | 3.3 | 3.0 | 4.6 | 3.9 |
| $CO + CO_2$ | mol % | 5.4 | 5.0 | 5.7 | 5.3 | 6.3 | 6.1 |
| Reaction time | min. | 65 | 72 | 60 | 75 | 73 | 68 |
| Color test according ASTM-D 1209-62: | | | | | | | |
| Molten trimellitic anhydride | Hz | 60 | 80 | 60 | 60 | 200 | 150 |
| Resin test | Hz | 20 | 40 | 20 | 20 | 70 | 60 |

What is claimed is:

1. A process for the preparation of trimellitic acid comprising catalytically oxidating pseudocumene with air in acetic acid as a solvent and in the presence of cobalt, manganese, cerium, titanium and bromine as a catalyst.

2. The process according to claim 1 wherein the total metal concentration, comprising cobalt, manganese, cerium and titanium, is between 0.1 and 1 percent by weight, relative to the pseudocumene.

3. The process according to claim 2 wherein the titanium content is between 0.5 and 10 percent by weight, relative to the total metal concentration.

4. The process according to claim 3 wherein the cobalt content is between 20 and 60 percent by weight, relative to the total metal concentration.

5. The process according to claim 4 wherein the manganese content is between 10 and 50 percent by weight, relative to the total metal concentration.

6. The process according to claim 5 wherein the cerium content is between 5 and 30 percent by weight, relative to the total metal concentration.

7. The process according to claim 6 wherein 0.05 to 0.7 percent by weight of bromine is employed, relative to pseudocumene.

8. The process according to claim 7 wherein the ratio of acetic acid to pseudocumene is between 1 to 1 and 4 to 1.

9. The process according to claim 8 wherein the reaction is carried out at a reaction temperature between 140° and 240° C. and at a pressure between 5 and 30 bars.

10. The process according to claim 2 wherein the cobalt content is between 20 and 60 percent by weight, relative to the total metal concentration.

11. The process according to claim 2 wherein the manganese content is between 10 and 50 percent by weight, relative to the total metal concentration.

12. The process according to claim 2 wherein the cerium content is between 5 and 30 percent by weight, relative to the total metal concentration.

13. The process according to claim 1 wherein 0.05 to 0.7 percent by weight of bromine is employed, relative to pseudocumene.

14. The process according to claim 1 wherein the ratio of acetic acid to pseudocumene is between 1 to 1 and 4 to 1.

15. The process according to claim 1 wherein the reaction is carried out at a reaction temperature between 140° and 240° C. and at a pressure between 5 and 30 bars.

* * * * *